(12) United States Patent
Neftel (10) Patent No.: US 10,792,409 B2
(45) Date of Patent: Oct. 6, 2020

(54) PERITONEAL DIALYSIS TREATMENT SYSTEM AND METHOD OF OPERATION

(71) Applicant: Debiotech S.A., Lausanne (CH)

(72) Inventor: Frédéric Neftel, Lausanne (CH)

(73) Assignee: Debiotech S.A., Lausanne (CH)

( * ) Notice: Subject to any disclaimer, the term of this patent is extended or adjusted under 35 U.S.C. 154(b) by 246 days.

(21) Appl. No.: 15/573,492

(22) PCT Filed: Jun. 2, 2016

(86) PCT No.: PCT/IB2016/053241
§ 371 (c)(1),
(2) Date: Nov. 13, 2017

(87) PCT Pub. No.: WO2016/193930
PCT Pub. Date: Dec. 8, 2016

(65) Prior Publication Data
US 2018/0117234 A1    May 3, 2018

(30) Foreign Application Priority Data

Jun. 3, 2015    (EP) ..................................... 15170614

(51) Int. Cl.
*A61M 1/28*    (2006.01)
*G16H 50/50*    (2018.01)

(52) U.S. Cl.
CPC ............ *A61M 1/282* (2014.02); *G16H 50/50* (2018.01); *A61M 2205/3341* (2013.01); *A61M 2205/3344* (2013.01); *A61M 2205/3379* (2013.01); *A61M 2205/50* (2013.01); *A61M 2205/502* (2013.01); *A61M 2205/52* (2013.01);
(Continued)

(58) Field of Classification Search
CPC ........ A61M 1/28; A61M 1/282; A61M 1/281; A61M 2205/128
See application file for complete search history.

(56) References Cited

U.S. PATENT DOCUMENTS 6,228,047 B1 * 5/2001 Dadson ............... A61M 1/1656
604/29
8,585,635 B2 * 11/2013 Degen ................. A61M 1/285
604/29
(Continued)

FOREIGN PATENT DOCUMENTS

EP    0471000 B1    2/1990
EP    1195171 B1    4/2002
(Continued)

OTHER PUBLICATIONS

Fischbach, M., et al. "Use of intraperitoneal pressure, ultrafiltration and purification dwell times for individual peritoneal dialysis prescription in children." Clinical nephrology vol. 46, Iss. 1, 1996, pp. 14-16.
(Continued)

*Primary Examiner* — Laura A Bouchelle
(74) *Attorney, Agent, or Firm* — Andre Roland S.A.; Nikolaus Schibli (57) ABSTRACT

The invention relates to a system which is a device suitable for carrying out removal of a dialysate volume fraction during a stasis phase so as to optimize ultrafiltration, the safety of the patient, the comfort of the patient, and/or the operation of the cycler.

26 Claims, 3 Drawing Sheets

(52) U.S. Cl.
CPC ..... *A61M 2230/06* (2013.01); *A61M 2230/42* (2013.01); *A61M 2230/63* (2013.01)

(56) References Cited

U.S. PATENT DOCUMENTS

| | | | |
|---|---|---|---|
| 2007/0112297 A1* | 5/2007 | Plahey | A61M 1/288 604/28 |
| 2010/0204765 A1* | 8/2010 | Hall | A61F 7/12 607/105 |
| 2012/0209085 A1 | 8/2012 | Degen et al. | |
| 2014/0031631 A1 | 1/2014 | Hall et al. | |

FOREIGN PATENT DOCUMENTS

| | | |
|---|---|---|
| EP | 1648536 B1 | 4/2008 |
| JP | 2012517298 | 8/2012 |
| JP | 2014512890 | 5/2014 |
| WO | WO 199906082 | 2/1999 |
| WO | WO1999051287 | 10/1999 |
| WO | WO2005009511 A2 | 2/2005 |
| WO | WO2005009512 | 2/2005 |
| WO | WO2007085993 | 8/2007 |
| WO | WO2014020501 | 2/2014 |
| WO | WO2016095026 A1 | 6/2016 |

OTHER PUBLICATIONS

International Search Report for PCT/IB2016/053241, dated Sep. 14, 2016.
Written Opinion of the International Searching Authority for PCT/IB2016/053241, dated Sep. 14, 2016.
Japanese Office Action dated Mar. 11, 2020 for Application N° JP2017-561917—With English translation.

* cited by examiner

PERITONEAL DIALYSIS TREATMENT SYSTEM AND METHOD OF OPERATION

CROSS REFERENCE TO RELATED APPLICATIONS

The present application is a United States national stage application of International Patent Application PCT/IB32016/053241 filed on Jun. 2, 2016 designating the United States, and claims foreign priority to European patent application EP 15170614.0 filed on Jun. 3, 2015, the contents of both documents being herewith incorporated by reference in their entirety.

FIELD OF THE INVENTION

The present invention relates to a dialysis system suitable for withdrawing a dialysate volume fraction from the peritoneal cavity of a patient under treatment, during a stasis phase, so as to optimize the treatment (for example the ultrafiltration), the safety of the patient, the comfort of the patient and/or the operation of the system.

The invention also relates to a method for improving the peritoneal dialysis treatment, the safety and/or the comfort of the patient during the treatment.

PRIOR ART

Peritoneal dialysis is a therapeutic means of purifying the blood. It allows impurities such as urea and excess water to be eliminated from a patient suffering from renal insufficiency, which impurities would usually have been eliminated from their body by kidneys that function normally. This therapeutic means makes use of the patient's peritoneum. The peritoneal membrane has a very large surface area and comprises a great many blood vessels. It thus acts as a natural filter between the blood and any liquid (the dialysate) potentially present in the peritoneal cavity. Numerous patents and patent applications disclose systems for performing peritoneal dialysis treatments, such as the documents EP 1 648 536 A2, EP 0 471 000 B1, EP 1 195 171 B1, EP 1 648 536 B1, which are incorporated by reference into the present description.

Treatment by peritoneal dialysis is relatively simple and comprises at least one cycle of three distinct phases:
- the "fill" (also called the filling phase): the system injects dialysate into the patient's peritoneal cavity;
- the "dwell" (also called the stasis phase): the system leaves the dialysate in the peritoneal cavity for a determined length of time;
- the "drain" (also called the drainage phase): the system withdraws the dialysate present in the peritoneal cavity.

In the present document, a phase may be a fill, a dwell or a drain (it being possible for each phase to be complete or partial), and a complete cycle comprises a fill, a dwell and a drain. The first cycle may comprise only a drainage phase when the last cycle of the preceding treatment comprised only a filling phase. Treatment may comprise several cycles. In other words, the phases may be repeated several times during one and the same treatment.

Systems generally referred to as APD (automated peritoneal dialysis) devices are designed to perform several fill, dwell and drain phases succeeding one another, in other words several cycles succeeding one another during one and the same treatment. This type of system thus performs a treatment over a number of hours. APD devices are thus particularly suitable for use during the night and/or at the patient's home.

During the dwell, the dialysate injected into the patient's peritoneal cavity changes over time, its composition is modified due to the exchange of components across the peritoneal membrane, and its volume varies according to the efficiency of the ultrafiltration, that is to say the quantity of liquid removed from the patient (e.g. water) and/or reabsorbed by said patient. Accordingly, the intraperitoneal pressure varies during the treatment. This pressure is linked in particular to the quantity of liquid present in the peritoneal cavity. The greater the volume of dialysate injected during the fill phase, the greater will be the initial pressure, and likewise the more efficient will be the ultrafiltration during the stasis phase, and the more the pressure will increase during this phase. However, beyond a certain threshold, the more the intraperitoneal pressure increases, the less the ultrafiltration will be able to be effected. Various publications deal with this subject, especially that of Dr. Michel Fischbach "Use of intraperitoneal pressure, ultrafiltration and purification dwell times for individual peritoneal dialysis prescription in children" (Clinical nephrology 1996 July; 46 (1): 14-6).

At the clinical level, it is desirable to use a large volume of dialysate during a long dwell time in order to improve the ultrafiltration, but the intraperitoneal pressure will be heavily impacted and, beyond a certain pressure threshold, the ultrafiltration will not be effective. In addition, the higher the intraperitoneal pressure, the greater a feeling of discomfort felt by the patient, and too high an intraperitoneal pressure may reduce the vital capacity of the patient and/or affect his health by substantially reducing, for example, the pulmonary reserve volume. Thus, the intraperitoneal pressure makes it possible to estimate the tolerance of the intraperitoneal volume and also to optimize the ultrafiltration. Accordingly, the volume of dialysate injected during the fill phase and/or the intraperitoneal pressure (which varies during the stasis phase) are important data. This pressure may also vary when the patient moves, breathes or gets up. For example, the pressure increases when the patient inhales and decreases when the patient exhales. Similarly, the pressure will vary with the movements of the patient, for example when the patient moves, turns in bed, gets up, sits down, coughs, sneezes, etc.

Some devices of the prior art limit the quantity of dialysate injected during the fill phase, so that the intraperitoneal pressure (during the stasis phase) remains below a threshold beyond which a feeling of discomfort to the patient would be generated. This suggests that the system is capable of predicting the variation in the intraperitoneal pressure during the stasis phase. This prediction is complex and often ineffective, since every patient is different and the intraperitoneal pressure can also vary depending on the patient's state of health or blood volume.

Other systems of the art measure the intraperitoneal pressure continuously in order to keep this pressure within a given range. Thus, during the fill phase, the system injects the dialysate into the cavity until the intraperitoneal pressure reaches a certain value. During the stasis phase, the system continuously monitors this pressure, withdraws dialysate when the intraperitoneal pressure exceeds an upper threshold, and re-injects dialysate when this pressure reaches a lower threshold. These systems thus perform a large number of operations during the stasis phase, causing a substantial variation in the volume of dialysate in the cavity throughout the stasis phase, thereby creating some uncertainty as to the actual efficiency of the ultrafiltration. Especially when the patient moves, for example while sleeping, the system will detect a pressure variation that will not be due to the ultrafiltration and the system will then re-inject or withdraw dialysate, and, when the patient returns to the initial position, the system will then perform the reverse operation.

GENERAL DESCRIPTION OF THE INVENTION

The invention presented in this document introduces greater intelligence to a dialysis system in order to improve the efficacy of the treatment, the comfort and safety of the patient and/or the operation of the system. The invention is of particular interest for APD systems used overnight or at the patient's home, since in both of these cases it is not necessary for a physician to be close to the system in order to initiate the withdrawal of a volume of dialysate during the stasis phase.

The system of the invention is adapted so as to allow the withdrawal of a given volume of dialysate present in the patient's peritoneal cavity during the stasis phase. One of the aims of the invention is to minimize the withdrawal of dialysate when the patient moves or more generally when the intraperitoneal pressure varies without this being due to an increase resulting from the ultrafiltration. Thus, the system can only order this withdrawal:
- after a certain period of time has elapsed since the start of a stasis phase, and/or
- during a defined time window, and/or
- at one or more specific moments during the stasis phase, and/or
- according to the profile of the intraperitoneal pressure (for example):
  - when the measured average of the intraperitoneal pressure exceeds a predetermined threshold and/or
  - there is an upward trend in the change of the intraperitoneal pressure; and/or
- as a function of a computer program taking into account a set of data or data type.

Figure 5:
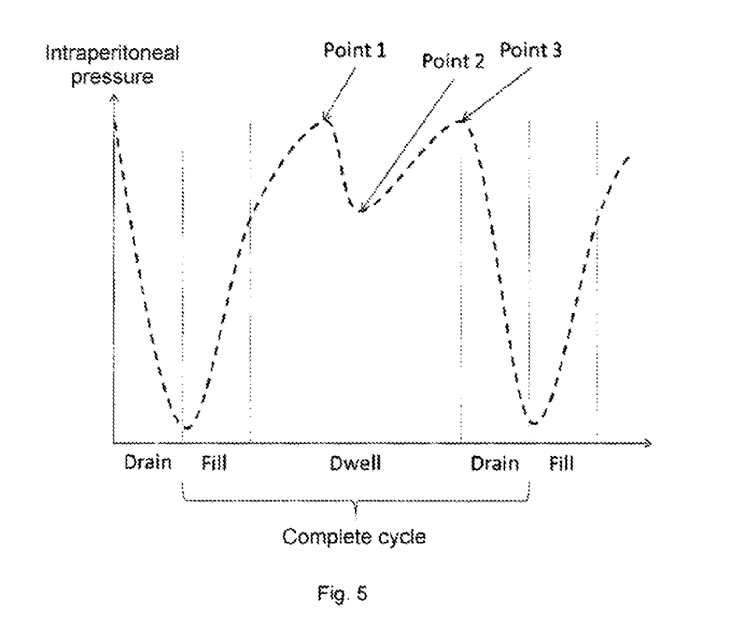

FIG. 5 shows a pressure profile during part of a dialysis treatment. The pressure data are linked to the intraperitoneal pressure of the patient. It will be noted from this graph that the intraperitoneal pressure changes over time during the stasis phase. This change of pressure may be substantially linked to the ultrafiltration. During the filling and drainage phases, the pressure variation is substantially due to the displacement of the dialysate into or out of the peritoneal cavity. Point 1 may be the moment when the partial withdrawal during the stasis phase is triggered, point 2 may be the moment when the partial withdrawal during the stasis phase is stopped, and point 3 may be the moment when the withdrawal of dialysate is triggered due to the start of the drainage phase. In this example, we can estimate that the withdrawn quantity of dialysate during the stasis phase substantially corresponds to the quantity of ultrafiltrate (produced between the start of the stasis phase and point 1 or 2) because the pressure level at point 2 is substantially at the same pressure level as at the end of the filling phase.

LIST OF THE FIGURES

The invention will be better understood hereinafter by means of a number of illustrated examples.

It goes without saying that the invention is not limited to these embodiments.

REFERENCE NUMBERS USED IN THE FIGURES 100 system
101 patient
102 cycler
103 cassette
104 container
105 container
106 controller (e.g. processor)
107 pump actuator
108 pressure sensor
109, 110, 111 other elements connected to the processors (screen, sensor, keyboard, button, etc.)
300 system
301 patient, peritoneal cavity
302 container holding usable dialysate
303 container holding used dialysate
304, 305, 306, 312 occlusion element (automatic valve, clamp, etc.)
307 pump
308, 309, 310 pressure sensor

DETAILED DESCRIPTION OF THE INVENTION

In the present document, the detailed description of the invention includes embodiments of devices, systems and methods which are given by way of illustration. Of course, other embodiments are conceivable and may be applied without departing from the scope or spirit of the invention. The detailed description that follows must therefore not be considered to be limiting.

Unless indicated otherwise, the scientific and technical terms used in the present document have the meanings commonly employed by persons skilled in the art. The definitions given in this document are mentioned with a view to making the frequently used terms easier to understand and are not intended to limit the scope of the invention.

The direction indications used in the description and the claims such as "top", "bottom", "left", "right", "upper", "lower", and other directions or orientations, are mentioned in order to provide greater clarity as regards the figures. These indications are not intended to limit the scope of the invention.

The verbs "have", "comprise", "include" or equivalent are used in this document in a broad sense and in general terms signify "includes, but is not limited to".

The term "or" is generally employed in a broad sense encompassing "and/or", unless the context clearly indicates the opposite.

Figure 1:
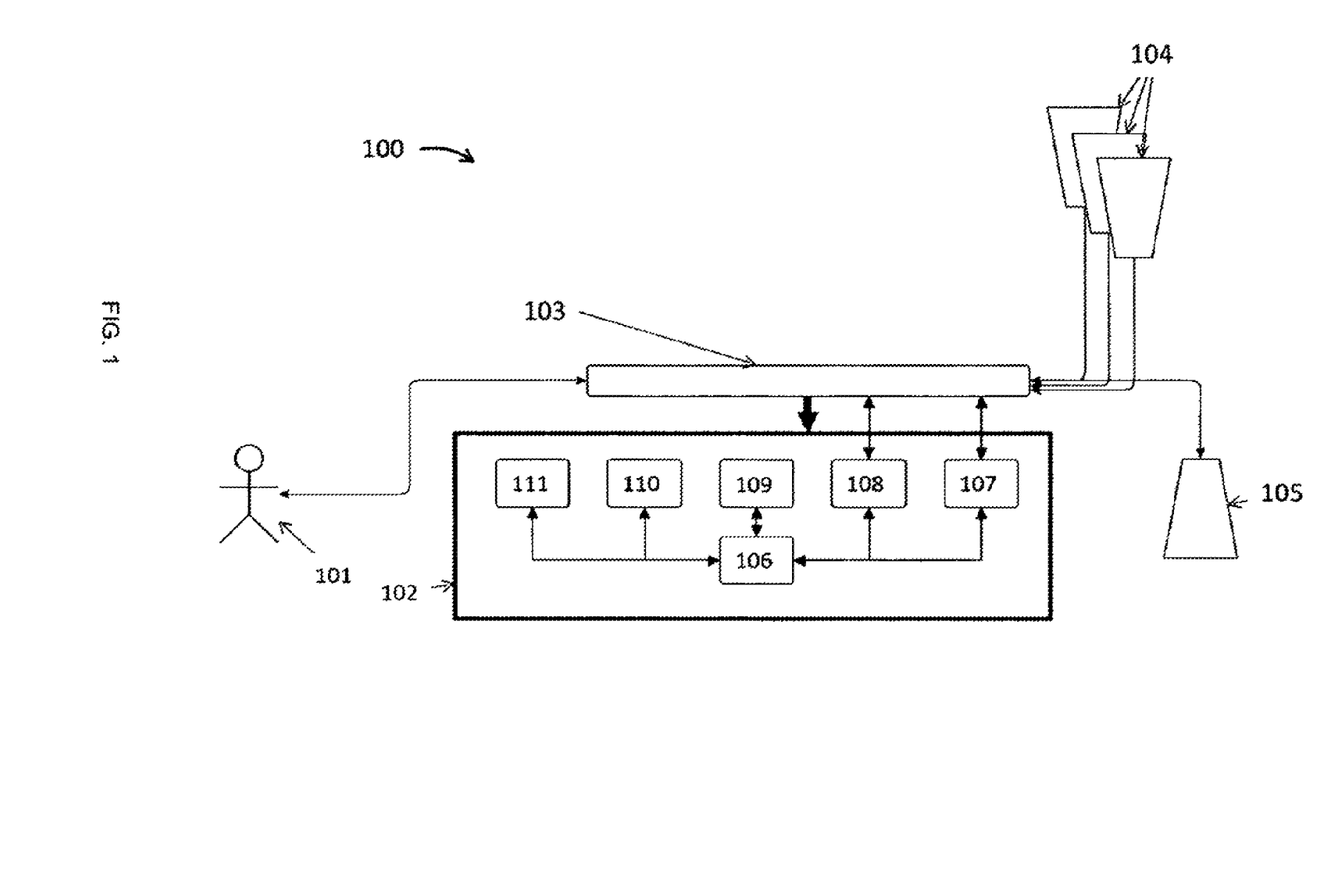
FIG. 1 is a schematic view of an embodiment of a dialysis system.

Dialysis Systems Suitable for the Invention:

According to an embodiment disclosed by FIG. 1, the system (100) comprises a cycler (102) designed to receive a disposable cassette (103) which is in fluidic communication with the patient's peritoneal cavity, and a reservoir adapted to contain dialysate (104, 105). For example, the system can include one or more bags (104) of fresh dialysate and/or one or more bags (105) of spent dialysate, which receive dialysate used by the treatment. The cycler can comprise actuating elements such as pump actuators (107) or valves. These actuating elements can be adapted to cooperate operationally (e.g. temporary mechanical coupling) with the disposable cassette (103), for example if the cassette comprises valves or a pumping system. A complete description is described in the international applications WO 99/51287 A1, WO 2005/009511 A2 and WO 2005/009512 A1, of which the entire content is incorporated by reference into the present document.

Disposable is to be understood as meaning that the cassette can be used only a certain number of times, for example, defines a single treatment compared to the cycler that can be reused several times, for example for several treatments. Thus, a cycler can be used in succession with several disposable cassettes.

The system comprises a sensor adapted to determine, measure or estimate a pressure associated with the intraperitoneal pressure. This sensor can be a pressure sensor in pressure communication with the peritoneal cavity. This sensor can be arranged as close as possible to the cavity, on the line connecting the patient to the cassette, or can be adapted to cooperate operationally (e.g. by temporary mechanical coupling) with the cassette. The embodiment shown in FIG. 1 has a pressure sensor (108) arranged in the cycler and cooperating with the cassette. The cassette (103) then comprises a specific zone with a membrane so as to transfer the pressure of the dialysate to the pressure sensor (108). A complete description is described in the international applications WO 2007/085993 A1 and WO 2014/020501 A1, of which the entire content is incorporated by reference into the present document. Preferably, this specific zone is in pressure communication and/or in fluidic communication with the peritoneal cavity. Thus, the pressure sensor can measure the pressure of a fluid in fluidic communication or pressure communication with the fluid present in the peritoneal cavity of the patient.

Ideally, the pressure sensor measures the pressure of the fluid present in the intraperitoneal cavity. However, depending on the distance between the cavity and the sensor and/or depending on the materials used (more or less pliable tube, for example) between these two elements, it can happen that the pressure measured by the sensor is not exactly equal to the intraperitoneal pressure. This is particularly true when the pump is actuated (during the filling or drainage phase). In the stasis phase, the measured pressure can be a value substantially reflecting the intraperitoneal pressure. However, perfect measurement is not essential, since the system can function knowing only the change of the pressure. The reason for this is that, even if the pressure measured is not exactly that of the intraperitoneal pressure, the change of this pressure over time is ideally substantially identical or proportional or similar to the change in the measured pressure.

Thus, the system can simply measure a pressure associated with the intraperitoneal pressure. This measurement may be equal to the intraperitoneal pressure. However, if this is not the case, then the system can use a mathematical model to estimate a value relatively close to the intraperitoneal pressure or simply to assess the change in the pressure.

Other elements may be included in the system, such as a temperature sensor, a means for heating the dialysate, a graphical interface, an electronic controller (106) (for example a processor, a memory coupled to the processor, etc.).

Figure 2:
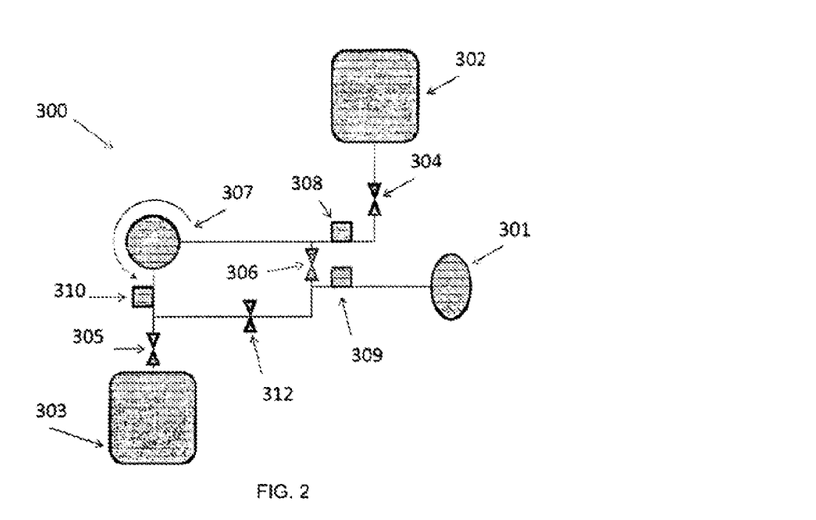
FIG. 2 is a schematic view showing the positioning of the elements of the system with respect to the dialysate circuit.

FIG. 2 illustrates the fluid path of a possible embodiment. The system (300) comprises at least one sensor (308, 309, 310) and a fluid-distributing device for fluidically connecting a supply of fresh dialysate (302), a patient (represented by the peritoneal cavity (301) thereof) and a reservoir of spent dialysate (303). The system is designed such that the dialysate flows:

from the supply of fresh dialysate (302) to the peritoneal cavity (301) of the patient,
from the peritoneal cavity (301) of the patient to the reservoir of spent dialysate (303).

A pump (307) and a set of valves (304, 312, 305, 306) controlled by a processor for automatically ordering movement of the dialysate and the distribution path of the dialysate. The pump can be a peristaltic pump and can be one-way.

For example, during a fill phase, some valves (304, 312) are open, while the other valves (306, 305) are closed and the pump is actuated. The pressure sensors (308, 309, 310) can monitor the pressure in the fluid path. During the stasis phase, the valves (304, 306, 312, 305) can be closed. In this embodiment, the pressure sensor (309) remains in pressure communication and fluidic communication with the peritoneal cavity (301) of the patient. During a drainage phase, the valve 304 is preferably closed, the valve 312 is closed, the valves 305 and 306 are open, and the pump (307) is actuated. The pressure sensors (308, 310, 309) can monitor the pressure in the fluid path.

The system processor can be adapted to execute a computer program. The system can additionally comprise an internal clock or a timing device such that the computer program can take account of a variable linked to time.

Method of Operation:

According to one aspect of the invention that may use a previously disclosed embodiment, the system comprises a processor and a sensor that are suitable for measuring a pressure associated with the intraperitoneal pressure (or at least for monitoring the change in the pressure) at least temporarily during a stasis phase. This monitoring will allow the system to withdraw a defined quantity of dialysate under certain conditions in order to ensure some comfort to the patient, to limit the undesirable or potentially harmful effects associated with an excessively high intraperitoneal pressure, and/or to substantially improve ultrafiltration.

In order to limit the withdrawals of dialysate that are caused by patient movement and/or by an exogenous disturbance, the system performs the monitoring and/or the withdrawal of dialysate during a stasis phase as a function of at least one following condition:

a predefined time window (that is to say a time frame whose start, end and/or duration can be predetermined) and/or
a change in the pressure and/or
the quantity of ultrafiltrate estimated at a given moment, and/or
a set of data processed by a computer program.

The data taken into account by the system or by the computer program of the system can be quantitative variables (pressure measurement, estimated quantity of ultrafiltrate, etc.), categorical variables (open or closed time window), discrete variables (random or non-random measurements) or continuous variables (continuous pressure measurement).

Figure 3:
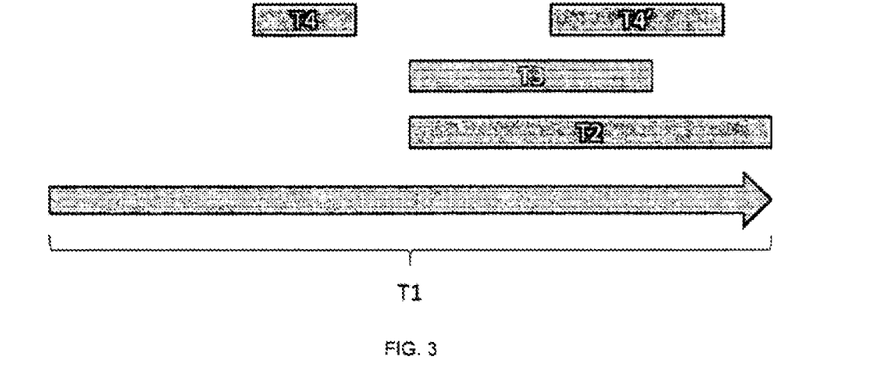
FIG. 3 shows the possible time windows.

Example of "Predefined Time Windows":

FIG. 3 shows different "predefined time windows". T1 represents an entire stasis phase: the start of this phase commences at the left-hand end of the arrow and the end of this phase terminates with the tip of the arrow. T2, T3, T4 and T4' represent "defined times" of this stasis phase during which the system is able to withdraw dialysate from the peritoneal cavity of the patient. If, during these defined times, the data collected and/or calculated by the processor exceed a determined threshold, the system will be able to perform (automatically for example) the withdrawal of a given quantity of dialysate during the stasis phase. To perform the withdrawal of the dialysate, the pump of the system can be used.

A time window can be defined as a time interval which can be predetermined, fixed or variable depending on one or more conditions. A time window can be characterized by an opening and/or a closure. That is to say, a time window can open at a predefined time $t_o$ and/or close at a predefined time $t_c$. Preferably, the system is adapted to open at least one time window at a moment $t_{o1}$ ($t_{o2}$, $t_{o3}$, etc., if there are several time windows) of a stasis phase.

During this defined time interval, but not exclusively, the system can evaluate a set of data, for example the average pressure for a given filling volume, which makes it possible to overcome the instantaneous variations, and more particularly the instantaneous variations that are produced outside this time interval. During this defined time interval, the system can initiate the withdrawal of a dialysate volume fraction.

Thus, it will be possible for the withdrawal of a certain volume of dialysate to be ordered automatically according to the volume of liquid (dialysate injected during the filling phase plus ultrafiltrate produced during the stasis phase) in the patient's peritoneum. This also makes it possible not to limit the ultrafiltration when the volume of dialysate in the peritoneum is too great.

Of course, during one and the same cycle, several withdrawals may be performed at different times depending on the measured intraperitoneal pressure.

T2 is a time window that starts at a time $t_{o2}$. Thus, the time window T2 will open only after a certain period of time following the start of the stasis phase. According to the figure, T2 terminates at the end of the stasis phase. For example, T2 can commence 30 minutes after the start of the stasis phase. If the stasis phase lasts for 120 min, then the length of T2 will be 90 min. It is only during these 90 minutes that the system will, if necessary, be able to perform a withdrawal of dialysate. In other words, the patient will be able to move during the 30 minutes preceding this time window of 90 minutes without the system inadvertently triggering a dialysate withdrawal operation, which would risk making the treatment less effective.

T3 is a time window which (like T2) starts after a certain period of time has elapsed following the start of the stasis phase. However, T3 is a shorter time window than T2, since T3 terminates before the end of the stasis phase. Thus, the system cannot perform withdrawal of dialysate, after this time window has closed, until the end of the stasis phase.

In the third example, the period during which the system can make adjustments consists of two time windows T4 and T4'. Their duration is different, and their time of activity is also different and spread over one and the same stasis phase.

Preferably, the duration of a time window is strictly less than the duration of the stasis phase which comprises this time window. In other words, the duration of the time window is equal to 1/x of the duration of the stasis phase, where x is strictly greater than 1. Furthermore, the same goes for the total duration of all the time windows of one and the same stasis phase.

If the treatment comprises several stasis phases, the system can open several time windows at identical or different times of each stasis phase.

In one embodiment, the time window can be fixed or variable for a stasis phase. For example, if the time window is initially 90 minutes, but during these 90 minutes the system performs one or more withdrawals of dialysate, then the system can decide to reduce the time window to 75 minutes on the principle that, during the remaining time, there is an insufficient probability of the intraperitoneal pressure again reaching the threshold caused by the ultrafiltration. Thus, the patient will be able to move and breathe, without inadvertent triggering, after the end of the shortened time window.

The system can provide the patient with a visual or acoustic warning when these defined times are active, and therefore the patient will be able to choose to make a certain movement outside of these defined times.

For example, the system can comprise and display a recommendation screen "Do not move during the measurements" or "Measurement in progress" or "Evaluation of the intraperitoneal pressure", etc. In this way, the patient is informed that the system is evaluating whether or not to perform a partial withdrawal of the dialysate.

According to an operating mode compatible with the above, the patient can voluntarily open a time window. In other words, the patient is able to define a time window, for example if he starts feeling some discomfort. However, it is preferably the system that will be able to decide, on the basis of the sensor data and/or a data set (which may be pressure), whether or not to initiate the withdrawal of a certain volume of dialysate.

Conversely, the patient can temporarily close a time window that would be opened by the system, so that the patient is able to move freely during this temporary closure (temporary deactivation). The system can reopen the time window after a determined period (specified by the patient or by the system); the duration of the temporary closure can change the time $T_c$ of the definitive closure of the modified time window. To facilitate this operation, the system can comprise an actuation control on the cycler (e.g. button or touch screen) or on a remote control separate from the cycler but coupled to the latter (by wire or wirelessly).

According to one possible embodiment, the system can also monitor the change in the pressure outside these time windows but can perform withdrawal of dialysate only during the time windows. In other words, the processor takes into account or monitors a data set, for example at least two pressure measurements, the change in pressure, the average pressure and/or the pressure profile during all or part of a stasis phase (or several stasis phases) and activates the pump (or authorizes the partial withdrawal of the dialysate) only during open time windows.

Monitoring the Pressure:

As explained above, the systems of the prior art trigger the withdrawal of a fraction of the dialysate during a stasis phase as soon as a single and unique value exceeds a threshold, for example as soon as the intraperitoneal pressure exceeds a threshold. However, consideration of a single and unique value is not desirable since it leads to inadvertent triggering of the withdrawal of dialysate during the stasis phase.

Given that the intraperitoneal pressure varies according to numerous phenomena (exogenous and/or endogenous), it may be necessary to take account not of one pressure value but of a set of data in order to filter the physiological variations or the variations linked to movements of the patient or other phenomena. Ideally, account should be taken only of stable measurements that are linked to a time when the patient is motionless. In other words, the instantaneous and/or parasitic variations in pressure must be discarded or at least should not be taken into account.

To ensure that the system of the invention does not perform inadvertent withdrawal of dialysate, the system monitors or takes into account a set of data. This set of data allows the system not to inadvisably trigger the withdrawal of dialysate during the stasis phase. Indeed, the system will order the withdrawal only if this is necessary. For this purpose, the system can use a processor that takes into account several data. For example, at least two measurement values of the sensor (for example those of the sensor 309 of FIG. 2) can be analyzed by the processor.

Thus, the system can take into account several values linked to the intraperitoneal pressure. These values can be the measurements of the pressure sensor, for example continuous and random measurements of the pressure peaks (positive and/or negative or minimum and/or maximum). As regards the pressure peaks, the system is able to define times, where each time may comprise two peaks which may be opposite. To discern these peaks, the system can use the first and/or second derivatives of the measured pressure curve. Or more simply, during a defined time period, the system can define a maximum value and/or a minimum value.

According to one mode of operation, the mathematical model can take into account a pressure measurement effected at a predefined time (for example at the end of the filling phase preceding the stasis phase or at the start of the stasis phase). This measurement can be used as a reference value for calculating a pressure threshold or a pressure gradient for initiating the partial withdrawal of the dialysate. Thus, in this case, the system uses a mathematical model using at least two values, a reference value and a measurement value at a time t during the stasis phase, which is compared (for example) to the reference value.

The system can also use a mathematical model taking account of these values. For example, the mathematical model can calculate an average. This average can be an average of the pressure data during a cycle, for example during a breathing cycle (inhalation+exhalation) of the patient, or any other time cycle; for example, a cycle can be between two maximum and/or minimum pressure peaks or it can also be a moving average.

Figure 4:
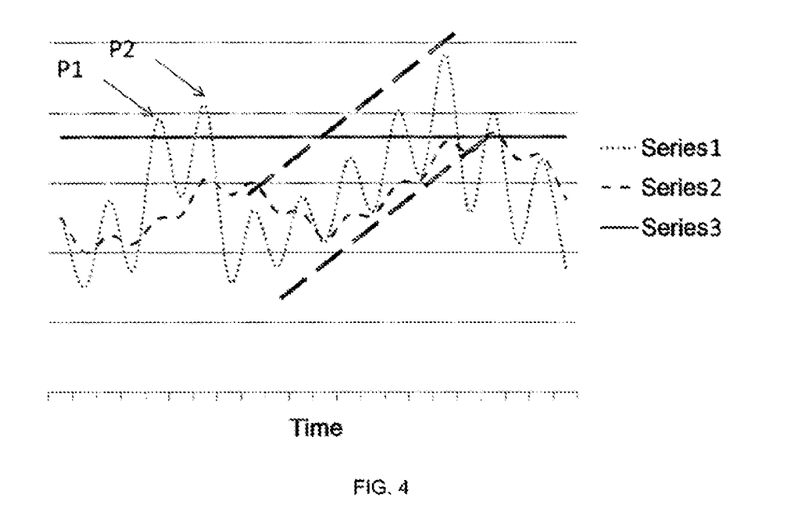
FIGS. 4 and 5 illustrate pressure profiles.

For example, FIG. 4 shows three series of data, with the first series of data being represented by the dotted curve. These are here raw measurement data from the sensor. The second series of data, represented by a dashed curve, shows, for example, a moving average of the sensor data over a predefined period. The third is a threshold. The devices of the prior art will trigger the withdrawal of some of the dialysate as soon as the dotted curve reaches or exceeds the threshold, i.e. many times during the stasis phase. Thus, these devices risk withdrawing too much dialysate during a single stasis phase, which will have a substantial impact on the effectiveness of the treatment. The device of the invention will only trigger the withdrawal, for example, if the dashed curve reaches or exceeds the threshold. In this example, the device will perform only a single withdrawal in such a way as to optimize the ultrafiltration and patient safety or comfort.

According to another operating mode (which can be used with this), another way to initiate the triggering of the partial withdrawal may be to monitor the trend in the evolution of the pressure; thus the mathematical model can be adapted to define a trend in the evolution of the pressure in such a way as to automatically control a partial withdrawal of the dialysate during the stasis phase. For example, points P1 and P2 (FIG. 4) do not represent a trend; it is likely only that pressure peaks may be due to the movement or movements of the patient. By contrast, after these two pressure peaks, the curve of the pressure measurements follows an upward trend between the two parallel lines, which is characteristic of an average increase of the intraperitoneal pressure caused by ultrafiltration. By virtue of this method, the system can determine whether or not to perform the withdrawal of dialysate.

Monitoring of the trend may make it possible to distinguish pressure variations that would not be due to the ultrafiltration. Thus, the mathematical model could take into account a set of values in such a way as to calculate a trend in the evolution of the pressure, for example by using the statistical models known to a person skilled in the art, such as the regression models (linear, multiple linear, polynomial, non-parametric generalized linear, multiple postulated and non-postulated, circular, elliptical or local, etc.), a method of least squares, standard deviation, variance, mathematical expectation, etc. By virtue of this mathematical model, the system could also help predict when it would be appropriate to carry out a partial withdrawal of dialysate. In other words, this mathematical model could predict a time to perform a partial withdrawal in order to define a time window (for example $t_o$, $t_c$ or duration) as discussed above.

The system can also take account of another value that would be linked directly or indirectly to the intraperitoneal pressure, such as the temperature of the environment or of the patient (in this case, the system can comprise a temperature sensor), the activity of the patient (for example depending on the time, sleep, etc.), his state of health or his profile (which could be input prior to the treatment via the user interface (illness, age, sex, maximum or acceptable volume for the patient's peritoneum, etc.)) etc.

Volume of Dialysate or Ultrafiltrate:

During the partial withdrawal, the systems of the prior art monitor the pressure in order to stop the withdrawal as soon as the pressure measurement reaches a predefined threshold. However, in the same way as for the triggering of the withdrawal, the pressure is not a sufficiently reliable datum since it varies too much depending on various phenomena. Thus, in order to overcome these flaws, the system of the invention can take into account a volume of ultrafiltrate produced at a given moment or can determine or estimate a volume of dialysate to be withdrawn or can withdraw a predefined volume of dialysate during the stasis phase.

Thus, the system of the invention can withdraw a predefined quantity of dialysate. This quantity can be a certain volume, for example 400 ml, or a percentage of dialysate injected, for example 20% of the dialysate injected during a preceding fill phase, it being possible for this percentage to be between 0 and 100%, preferably between 5 and 50%. This quantity can be determined by the physician or estimated by the system by taking into account the trend of the pressure curve or the aforementioned reference value or according to the patient data (patient profile, state of health, characteristics of the peritoneum, of the dialysate (glucose level), efficacy of the treatment, compliance with the treatment, etc.).

The system can thus be adapted to calculate or estimate the volume (or quantity) of ultrafiltrate present (or produced) in the peritoneal cavity at a given moment, for example just before or during the withdrawal. This quantity can be an estimate based on a mathematical model. This mathematical model can be used to calculate a volume of ultrafiltrate over time or a trend. This mathematical model can take into account empirical data, a data table, or any other data cited above.

This volume fraction to be withdrawn during the stasis phase can take account of this estimate to withdraw:

a volume of dialysate equal (substantially) to the estimated quantity of ultrafiltrate at a time t, or a greater volume of dialysate than the ultrafiltrate, or a smaller volume of dialysate than the ultrafiltrate.

The mathematical model can also take into account the time remaining before the end of the stasis phase.

In addition, this datum can also be taken into account by the system (for example a mathematical model) for initiation of the withdrawal. Thus, the system could initiate the withdrawal as soon as the estimated volume of ultrafiltrate produced exceeds a certain threshold or as soon as the estimated volume of liquid present in the patient's peritoneum exceeds a predetermined threshold.

Example of Possible Methods or Products According to the Invention:

The following list of products or methods are non-limiting examples. It goes without saying that the invention is not limited to these embodiments and that various embodiments can be combined in order to improve the characteristics thereof.

According to one embodiment, the invention relates to a method which comprises the following steps:
  making available a system comprising:
    a dialysate circuit adapted to be fluidically connected to the peritoneal cavity of the patient during the dialysis treatment,
    a pumping device adapted for causing dialysate to flow through the dialysate circuit to or from the peritoneal cavity of the patient,
    a sensor adapted for measuring the pressure of the dialysate, the sensor being configured in such a way as to measure a pressure linked to the intraperitoneal pressure during a stasis phase,
    a processor coupled to the pump and to the sensor,
    a computer program that can be executed by the processor and takes account of the measurement values from the sensor,
  sending the measurement values from the sensor to the processor
  executing the computer program
  initiating the withdrawal of a dialysate volume fraction from the peritoneal cavity during a stasis phase, according to the result of the computer program.

The computer program can use a mathematical model taking into account several values linked to the pressure measurement during a stasis phase (more than two measurement values, or even more than three measurement values). These can be the pressure values measured by the sensor adapted to measure the pressure of the dialysate. The mathematical model can take into account:
  only the measurement values during a determined time, or
  only the one or more extreme measurement values during one or more defined times during one and the same stasis phase. For example, the mathematical model can take into account the pressure peaks (minimum and/or maximum, positive and/or negative), and in this case a time can contain two opposite peaks (one minimum and one maximum or one positive and one negative).

The mathematical model can calculate an average of the measurement values taken into account; this average can be a moving average.

The computer program can take into account a time window during which the system is allowed to initiate the withdrawal during a stasis phase. The time window can be characterized by a predetermined opening, a predetermined closing and/or a predetermined duration.

The computer program is able not to take account of variations in values that would be due to a movement of the patient, to the breathing of the patient or to the beating of the patient's heart.

The computer program can take into account an estimate of the ultrafiltration at the moment of program execution.

The method can additionally comprise at least one of the following steps:
  measuring the pressure at the end of the filling phase or start of the stasis phase,
  registering this value in a memory of the system, this value being considered as a reference value,
  comparing this reference value to other values linked to the pressure of the dialysate during the stasis phase,
  calculating a pressure threshold as a function of this reference value,
  calculating a pressure gradient as a function of this reference value,
  initiating the withdrawal as soon as a value linked to the pressure of the dialysate reaches the calculated pressure threshold or the calculated pressure gradient.

According to one embodiment (which may be compatible with the preceding embodiment), the invention relates to a computer program product comprising a computer code which, when executed in a peritoneal dialysis system, is designed to order a withdrawal of a volume fraction of dialysate contained in the peritoneum of a patient with kidney failure during a stasis phase, the computer program product taking into account a set of data comprising at least one value associated with the intraperitoneal pressure of the patient.

The computer program product can comprise a mathematical model that takes account of several pressure measurements associated with the intraperitoneal pressure of the patient. The mathematical model can be adapted to distinguish the pressure variations that would be due to a movement of the patient, to the breathing of the patient or to the beating of the patient's heart.

Said data set can additionally comprise a variable linked to a time window during which the computer program product can initiate the withdrawal during a stasis phase.

Said data set can additionally comprise a variable linked to the estimate of the volume of the or a fluid in the peritoneum of the patient at a given time, for example the total volume or the ultrafiltrate volume.

At least one value associated with the intraperitoneal pressure can be a pressure measurement carried out at the end of a filling phase or at the start of a stasis phase, said pressure measurement being used by the computer program product as the reference value, which can be used to calculate a pressure threshold or a pressure gradient.

According to one embodiment (which may be compatible with at least one of the preceding embodiments disclosed), the invention relates to a dialysis system adapted for providing peritoneal dialysis treatment to a patient with kidney failure, which system can comprise a cycler in which is arranged a processor adapted to execute a computer program product as described above.

According to one embodiment (which may be compatible with at least one of the preceding embodiments disclosed), the invention relates to an automatic method of fluid withdrawal by a system which comprises: a dialysate circuit fluidically connected to the peritoneal cavity of a patient,
  a pump adapted to extract dialysate from the peritoneal cavity of the patient through the dialysate drainage circuit, a pressure sensor in pressure communication with the peritoneal cavity, and a processor connected to the pump and to the pressure sensor.

The method comprising the following steps:

sending the pressures measured by the pressure sensor to the processor, calculating, with the aid of the processor, an average of the measured pressures, initiating, by way of the processor, the withdrawal of a predefined quantity of dialysate from the peritoneal cavity of the patient as soon as the average of the measured pressures exceeds a predefined threshold.

According to one embodiment (which may be compatible with at least one of the preceding embodiments disclosed), the invention relates to an automatic method of fluid withdrawal by a system which comprises:

a dialysate circuit fluidically connected to the peritoneal cavity of a patient, a pump adapted to extract dialysate from the peritoneal cavity of the patient through the dialysate drainage circuit, a pressure sensor in pressure communication with the peritoneal cavity, a memory, a processor connected to the pump, the memory and the pressure sensor.

This system can be adapted to perform on the patient peritoneal dialysis treatment comprising at least one filling phase (fill) and one stasis phase (dwell).

The method additionally comprises the following steps:

taking, and registering in the memory, a first pressure measurement at the start of the stasis phase, taking an additional pressure measurement during the stasis phase, calculating, with the aid of the processor, the difference between the first pressure measurement and the additional pressure measurement, initiating, by way of the processor, the withdrawal of a predefined quantity of dialysate from the peritoneal cavity of the patient as soon as the calculated difference exceeds a predefined threshold.

According to one embodiment (which may be compatible with at least one of the preceding embodiments disclosed), the invention relates to an automatic method of fluid withdrawal by a system which comprises:

a dialysate circuit fluidically connected to the peritoneal cavity of a patient, a pump adapted to extract dialysate from the peritoneal cavity of the patient through the dialysate drainage circuit, a pressure sensor in pressure communication with the intraperitoneal pressure, a memory, a processor connected to the pump, the memory and the pressure sensor.

The system can be adapted to perform peritoneal dialysis treatment comprising at least one filling phase (fill) and one stasis phase (dwell).

The method additionally comprises the following steps:

sending the measured pressures to the processor, opening a time window whose duration and/or time of opening and/or time of closing is predefined during the stasis phase, during which the processor can initiate the withdrawal of a quantity of dialysate from the peritoneal cavity of the patient, initiating, by way of the processor, the withdrawal of a quantity of dialysate from the peritoneal cavity of the patient in accordance with an intraperitoneal pressure condition.

According to one embodiment (which may be compatible with at least one of the preceding embodiments disclosed), the invention relates to a system adapted for performing on a patient peritoneal dialysis treatment comprising a filling phase (fill), a stasis phase (dwell) and a drainage phase (drain), which system comprises:

a dialysate circuit fluidically connected to the peritoneal cavity of a patient, a pump adapted to extract dialysate from the peritoneal cavity of the patient through the dialysate drainage circuit, a pressure sensor in pressure communication with the intraperitoneal cavity, a processor connected to the pump and to the pressure sensor.

The processor is adapted to initiate a withdrawal of a quantity of dialysate in accordance with an intraperitoneal pressure condition, only during a time window at a predetermined moment of the stasis phase.

According to one embodiment (which may be compatible with at least one of the preceding embodiments disclosed), the invention relates to a system for performing on a patient peritoneal dialysis treatment comprising at least one filling phase (fill) and a stasis phase (dwell), which system comprises:

a processor;

a distribution device coupled to the processor and adapted to deliver a fluid to and/or withdraw a fluid from the peritoneal cavity of the patient; and a sensor coupled to the processor and to the distribution device and adapted to measure a pressure of a fluid in pressure communication with the peritoneal cavity of the patient.

The distribution device is adapted to perform the withdrawal of a quantity of fluid contained within the peritoneal cavity of the patient during a stasis phase.

In addition, the withdrawal during the stasis phase is initiated by the processor as soon as:

the average of the pressure measurements from the sensor reaches a predetermined threshold, or the measured pressure exceeds a threshold determined in accordance with the first pressure measurement performed at the start of the stasis phase.

The processor can initiate the withdrawal only during a predefined time window of the stasis phase.

The processor can monitor a trend in the evolution of the data measured by the sensor.

The processor can monitor the data measured by the sensor only during the defined time.

The defined time can be characterized by a duration shorter than the stasis phase.

The time window can open after a certain predefined period of time has elapsed following the start of the stasis phase.

The quantity of dialysate withdrawn can be a predefined volume of dialysate or a predefined percentage of the volume of dialysate injected during one or more preceding filling phases.

The quantity of dialysate withdrawn can be a function of the measured pressure and/or of the evolution of this pressure, optionally taking into account the total volume of dialysate injected during one or more filling phases.

The invention claimed is:

1. A method for performing peritoneal dialysis treatment on a patient by a dialysis system, the dialysis system including a dialysate circuit configured to be in fluidic connection with a peritoneal cavity of the patient, a pumping device configured to cause dialysate to flow through the dialysate circuit to or from the peritoneal cavity of the patient, a sensor configured to measure a pressure of the dialysate, and a processor operatively coupled to the pumping device and the sensor, the method comprising the steps of:
measuring a pressure representing an intraperitoneal pressure of the peritoneal cavity during a stasis phase with the sensor, the peritoneal cavity of the patient being in fluidic connection with the dialysate circuit during the entire stasis phase; and
initiating a withdrawal of a dialysate volume fraction from the peritoneal cavity during a time window of the stasis phase with the processor, according to a result of the measuring, the time window for initiating the withdrawal being shorter in duration than a duration of the stasis phase.

2. The method as claimed in claim 1, wherein the processor uses a mathematical model that considers several pressure measurement values during the stasis phase.

3. The method as claimed in claim 2, wherein the mathematical model only considers the several pressure measurement values during a determined time.

4. The method as claimed in claim 2, wherein the mathematical model only considers an extreme measurement value of a defined time period during the stasis phase.

5. The method as claimed in claim 2, further comprising the step of:
calculating an average of the several pressure measurement values by the mathematical model with the processor.

6. The method as claimed in claim 5, wherein the calculated average is a moving average.

7. The method as claimed in claim 1, wherein the time window includes at least one of a predetermined opening, a predetermined closing, and a predetermined duration.

8. The method as claimed in claim 1, wherein in the step of initiating, variations in values resulting from a movement of the patient, a breathing of the patient, or a heartbeat of the patient are not considered.

9. The method as claimed in claim 1, wherein in the step of initiating, an estimate of a volume of an ultrafiltrate at a moment of performance of the step of initiating is considered.

10. The method as claimed in claim 1, further comprising the steps of:
measuring the pressure at a predefined moment by the sensor; and
storing a value of the pressure in a memory of the dialysis system as a reference value.

11. The method as claimed in claim 10, wherein the predefined moment is at an end of a filling phase or a start of the stasis phase.

12. The method as claimed in claim 10, further comprising the step of:
comparing the reference value to other values linked to the pressure of the dialysate during the stasis phase.

13. The method as claimed in claim 10, further comprising the step of:
calculating a pressure threshold as a function of the reference value.

14. The method as claimed in claim 10, further comprising the step of:
calculating a pressure gradient as a function of the reference value.

15. The method as claimed in claim 10, further comprising the steps of:
calculating a pressure threshold as a function of the reference value or calculating a pressure gradient as a function of the reference value; and
initiating the withdrawal as soon as a value linked to the pressure of the dialysate reaches the calculated pressure threshold or the calculated pressure gradient.

16. The method as claimed in claim 1, wherein the time window for initiating the withdrawal begins after a certain period of a start of the stasis phase.

17. A non-transitory computer readable medium, the computer readable medium having computer instructions recorded thereon, the computer instructions configured to perform a method when executed on a computer device operatively connected to a peritoneal dialysis system, the method comprising the step of:
ordering a withdrawal of a dialysate volume fraction included in a peritoneum of a patient with kidney failure during a time window of a stasis phase, the peritoneal cavity of the patient being in fluidic connection with the dialysate circuit during the entire stasis phase, by considering a set of data including a value associated with an intraperitoneal pressure of the patient, the time window for initiating the withdrawal being shorter in duration than a duration of the stasis phase.

18. The non-transitory computer readable medium as claimed in claim 17, the method further comprising a step of:
considering several pressure measurements associated with the intraperitoneal pressure of the patient by a mathematical model with the step of ordering.

19. The non-transitory computer readable medium as claimed in claim 18, wherein the mathematical model is configured to distinguish pressure variations resulting from a movement of the patient, a breathing of the patient, or to a heartbeat of the patient.

20. The non-transitory computer readable medium as claimed in claim 18, wherein the set of data includes a variable linked to the time window.

21. The non-transitory computer readable medium as claimed in claim 18, wherein a value associated with the intraperitoneal pressure is a pressure measurement carried out at an end of a filling phase or at a start of the stasis phase, the pressure measurement used as a reference value.

22. The non-transitory computer readable medium as claimed in claim 21, wherein the reference value is used to calculate a pressure threshold or a pressure gradient.

23. The non-transitory computer readable medium as claimed in claim 17, wherein the time window for initiating the withdrawal begins of a certain period after a start of the stasis phase.

24. A dialysis system comprising:
a cycler configured to be in fluidic connection with a peritoneal cavity of a patient;
a pumping device configured to cause dialysate to flow through a dialysate circuit to or from the peritoneal cavity of the patient;
a sensor configured to measure a pressure of the dialysate; and
a processor operatively coupled to the pumping device and the sensor, processor configured to order a withdrawal of a dialysate volume fraction included in a peritoneum of the patient with kidney failure during a time window of a stasis phase, the peritoneal cavity of the patient being in fluidic connection with the dialysate circuit during the entire stasis phase, by considering a value associated with an intraperitoneal pressure of the patient, the time window for initiating the withdrawal being shorter in duration than a duration of the stasis phase.

25. The dialysis system as claimed in claim 24, further comprising:
   a user interface configured to allow a user to force an opening or a closing of the time window during which the processor can order the withdrawal of the dialysate.

26. The dialysis system as claimed in claim 24, wherein the time window for initiating the withdrawal begins after a certain period of a start of the stasis phase.

\* \* \* \* \*